US011504430B2

(12) United States Patent
Wickstrom et al.

(10) Patent No.: US 11,504,430 B2
(45) Date of Patent: Nov. 22, 2022

(54) ELUENT SOLUTION

(75) Inventors: Torild Wickstrom, Oslo (NO); Anders Svadberg, Oslo (NO); Ole Kristian Hjelstuen, Oslo (NO); Dag M Evje, Oslo (NO); Liane Ochsenfeld, Oslo (NO)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 13/997,808

(22) PCT Filed: Dec. 21, 2011

(86) PCT No.: PCT/EP2011/073670
§ 371 (c)(1),
(2), (4) Date: Jun. 25, 2013

(87) PCT Pub. No.: WO2012/089594
PCT Pub. Date: Jul. 5, 2012

(65) Prior Publication Data
US 2013/0324715 A1   Dec. 5, 2013

Related U.S. Application Data

(60) Provisional application No. 61/427,839, filed on Dec. 29, 2010.

(51) Int. Cl.
| | | |
|---|---|---|
| *A61K 51/00* | (2006.01) | |
| *A61M 36/14* | (2006.01) | |
| *A61K 47/12* | (2006.01) | |
| *C07B 59/00* | (2006.01) | |
| *B01J 19/00* | (2006.01) | |
| *C01B 9/08* | (2006.01) | |
| *C07C 51/363* | (2006.01) | |
| *A61K 51/04* | (2006.01) | |

(52) U.S. Cl.
CPC .......... *A61K 47/12* (2013.01); *A61K 51/0406* (2013.01); *B01J 19/00* (2013.01); *C01B 9/08* (2013.01); *C07B 59/00* (2013.01); *C07B 59/001* (2013.01); *C07C 51/363* (2013.01)

(58) Field of Classification Search
CPC .... A61K 47/12; A61K 51/0406; C07B 59/00; C07B 59/001; B01J 19/00; C01B 9/08; C07C 51/363
USPC ....................................................... 424/1.89
See application file for complete search history.

(56) References Cited

U.S. PATENT DOCUMENTS

| | | | |
|---|---|---|---|
| 5,425,063 A | | 6/1995 | Ferrieri et al. |
| 5,888,970 A * | | 3/1999 | Rajopadhye et al. ........ 424/1.69 |
| 8,269,035 B2 | | 9/2012 | Kurosaki et al. |
| 2006/0245980 A1* | | 11/2006 | Kiselev et al. .................. 422/130 |
| 2008/0076914 A1* | | 3/2008 | Grigg .................. A61K 51/0491 536/50 |
| 2008/0305042 A1* | | 12/2008 | Gacek et al. ................ 424/1.89 |
| 2010/0150835 A1 | | 6/2010 | Langstrom et al. |
| 2010/0225853 A1 | | 9/2010 | Veach et al. |
| 2010/0243972 A1 | | 9/2010 | Voccia et al. |
| 2010/0261931 A1 | | 10/2010 | Kurosaki et al. |

FOREIGN PATENT DOCUMENTS

| | | | |
|---|---|---|---|
| BE | WO 2008101305 A1 * | 8/2008 | .............. A61K 51/04 |
| EP | 2230229 | 9/2010 | |
| EP | 2230229 A1 | 9/2010 | |
| KR | 20080078233 A | 8/2008 | |
| KR | 1020080078233 | 8/2008 | |
| MX | 2008016344 A | 2/2009 | |
| MX | 2010006901 A | 9/2010 | |
| MX | 2010007398 A | 10/2010 | |
| RU | 2165266 C1 | 4/2001 | |
| RU | 2007115903 A | 12/2008 | |
| RU | 2394040 C2 | 7/2010 | |
| WO | WO 2007148088 A2 * | 12/2007 | |
| WO | 2009/0835530 | 7/2009 | |
| WO | WO-2009127372 A1 * | 10/2009 | .............. C07B 59/00 |
| WO | WO2010/060694 A1 | 6/2010 | |
| WO | WO 2010063403 A2 * | 6/2010 | |
| WO | WO-2011151283 A1 * | 12/2011 | ........... A61K 51/121 |

OTHER PUBLICATIONS

Jewett et al. Appl. Radiat. Isot. 1990, 41, 583-586.*
Hjelstuen et al. Eur. J. Pharm. Biopharm. 78 (2011) 307-313.*
Lee et al. J. Labelled Cmpd Radiopharm 2007, S165.*
Fang et al. J Nucl. Med. 2007, 325P.*
Padgett et al. Appl. Radiat. Isot. 1989, 40, 433-445. (Year: 1989).*
Lemaire et al. J. Label. Compd Radiopharm. 2002, 45, 435-447. (Year: 2002).*
PCT/EP2011/073670 ISRWO dated Mar. 27, 2012.
Chinese Office Action and Search Report dated May 5, 2016 in corresponding CN Appl. No. 201180063488.7 (English Translation of Office Action and Search Report attached).
Ming-Rong Zhang et al., "Development of an automated system for synthesizing 18F-labeled compounds using [18F] fluoroethyl bromide as a synthetic precursor," Applied Radiation and Isotopes, vol. 57, 2002, pp. 335-342.

(Continued)

*Primary Examiner* — Michael G. Hartley
*Assistant Examiner* — Sean R Donohue
(74) *Attorney, Agent, or Firm* — Culhane Meadows, PLLC; Jeff B. Vockrodt

(57) ABSTRACT

The present invention provides a novel method for the preparation of $^{18}$F-fluoride ($^{18}$F) for use in radiofluorination reactions. The method of the invention finds use especially in the preparation of $^{18}$F-labelled positron emission tomography (PET) tracers. The method of the invention is particularly advantageous where bulk solutions are prepared and stored in prefilled vials rather than being freshly prepared on the day of synthesis. Also provided by the present invention is a radiofluorination reaction which comprises the method of the invention, as well as a cassette for use in carrying out the method of the invention and/or the radiofluorination method of the invention on an automated radiosynthesis apparatus.

9 Claims, 4 Drawing Sheets

(56) References Cited

OTHER PUBLICATIONS

Russian Office Action dated Mar. 3, 2016 in corresponding Appl. No. 2013/126979. (English Translation attached).
Decision to Grant a Patent in corresponding Russian Application No. 2013125979/04 filed Dec. 21, 2011. (English Translation enclosed).
Office Action for Mexican Patent Appl. No. MX/a/2013/007699, dated Feb. 20, 2018, 8 pages, (4 Pages of English Translation + 4 Pages Official Copy).
Office Action for Korean Patent Appl. No. 10-2013-7017012, dated Mar. 2, 2018, 21 pages, (12 Pages of English Translation + 9 Pages Official Copy).
Korea Second Notice of Final Rejection corresponding to Korean Application No. 10-2013-7017012, dated Dec. 13, 2018.
Korea Notice of Preliminary rejection corresponding to KR Application No. 029250576 dated Apr. 23, 2019.
English Translation of KIPO Notice of Last Preliminary Rejection in Korean Patent Application No. 10-2019-7001271.
Chinese Office Action received in Application No. 201810077584.0 dated Jul. 3, 2020, 20 pages. (with translation).
Ackermann, et al., "Synthesis of 2-[(4-[18F]Fluorobenzoyloxy)methyl]-1,4-naphthalenedione from 2-hydroxymethyl 1,4-naphthoquinone and 4-[18F] fluorobenzoic acid using dicyclohexyl carbodiimide," Sep. 23, 2011, Wiley Online Library, Journal of Labelled Compounds and Radiopharmaceuticals, 7 pages.
Broadack, et al., "Robotic Production of 2-Deoxy-2-[18F]Fluoro-D-Glucose: A Routine Method of Synthesis Using Tetrabutylammonium [18F] Fluoride," Appl. Radiat. Isot. vol. 39, No. 7, Nov. 3, 1987, [no date] 1988, 5 pages.
Chin, "Developing Artificial Hydrolytic Metalloenzymes by a Unified Mechanistic Approach," Department of Chemistry, Mar. 12, 1991, 8 pages.
Hamacher, et al., "Efficient Stereospecific Synthesis of No-Carrier-Added 2-[18F]-Fluoro-2-Deoxy-D-Gluocose Using Aminopolyether Supported Nucleophilic Substitution," J. Nucl. Med. 27, [no date] 1986, 4 pages.
Yu, "Review of 18F-FDG synthesis and quality control," biij, Biomedical Imaging and Intervention Journal, Dec. 30, 2006, 11 pages.
Khalil, "Basic Sciences of Nuclear Medicine," Second Edition, Basic Sciences of Nuclear Medicine, [no date] 2011, 564 pages.
Kilbourn, et al., "Fluorine-18 Radiopharmaceuticals," Fluorine in Medicinal Chemistry and Chemical Biology, [no date] 2009, 28 pages.
Knust, et al., "Production of Fluorine-18 Using an Automated Water Target and a Method for Fluorinating Aliphatic and Aromatic Compounds," Appl. Radiat. Isot. vol. 37, No. 8, Int. J. Radiat. Appl. Instrum. Part A. 1986 [no date], 4 pages.
Knust, et al., "Synthesis, Quality Control and Tissue Distribution of 2-[18 F]-Nicotinic Acid Diethylamide, a Potential Agent for Regional Cerebral Function Studies," Journal of Radioanalytical Chemistry, vol. 74, No. 1 (1982), Jan. 28, 1981, 9 pages.
Kryza, et al., "Fully automated [18F] fluorocholine synthesis in the TracerLab MX FDG Coincidence synthesizer," Nuclear Medicine and Biology 35 (2008) 6 pages.
McConathy, et al., "Improved synthesis of anti-[18F]FACBC: improved preparation of labeling precursor and automated radiosynthesis," Applied Radiation and Isotopes 58 (2003) 10 pages.
Nanni, et al., "18F-FACBC Compared with 11C-Choline PET/CT in Patients with Biochemical Relapse After Radical Prostatectomy: A Prospective Study in 28 Patients," Clinical Genitourinary Cancer, vol. 12, No. 2, 5 pages.
Oh, et al., "Fully automated synthesis of [18F] fluoromisonidazole using a conventional [18F] FDG module," Nuclear Medicine and Biology 32, (2005), Jun. 14, 2005, 7 pages.
Oh, et al., "Fully automated synthesis system of 3'-deoxy-3'-[18F] fluorothymidine," Nuclear Medicine and Biology 31 (2004) Jan. 24, 2004, 7 pages.
Ruth, et al., "Absolute Cross Sections for the Production of 18F via the 18O 9p, n)18F Reaction," Radiochimica Acta 26, 1979, Jan. 29, 1979, 4 pages.
Rutherford, "Chemistry of Radiohalogens (F, Br. and I)," Molecular Imaging: Radiopharmaceuticals for PET and SPECT, 2009 [no date], 15 pages.
Schlyer et al., "Separation of [18 F]Fluoride from [18O] Water Using Anion Exchange Resin," Appl. Radiat. Isot. vol. 41, No. 6, 1990, Int. J. Radiat Appl. Istrum. Part A, Nov. 1989, 3 pages.
Schubiger, et al., "PET Chemistry: The Driving Force in Molecular Imaging," New York, NY: Springer, 2006, 1 page.
Snyder et al., "Chemistry of Fluorine-18 Radiopharmaceuticals," Radiochemistry and Applications, [No. date] 2003, 33 pages.
Sun, et al., "New approach to fully automated synthesis of sodium [18F] fluoroacetate-a simple and fast method using a commercial synthesizer," Nuclear Medicine and Biology 33, (2006) Jul. 7, 2005, 6 pages.
Nuts, et al., "The Role of Protective Groups in Organic Synthesis," Greene's Protective Groups in Organic Synthesis, Fourth Edition, [no date] 2007, 15 pages.

* cited by examiner

ELUENT SOLUTION

This application is a filing under 35 U.S.C. 371 of international application number PCT/EP2011/073670, filed Dec. 21, 2011, which claims priority to U.S. application No. 61/427,839 filed Dec. 29, 2010, the entire disclosure of which is hereby incorporated by reference.

TECHNICAL FIELD OF THE INVENTION

The present invention relates to the field of radiopharmaceuticals, and in particular to the preparation of compounds suitable for use in positron emission tomography (PET). A method useful in the synthesis of compounds labelled with $^{18}F$ is provided. Also provided by the present invention is a radiofluorination reaction which comprises the method of the invention and as a cassette for conveniently carrying out the method and the radiofluorination reaction of the invention.

DESCRIPTION OF RELATED ART

Nucleophilic substitution with [$^{18}F$]fluoride ($^{18}F^-$) is currently the most important route in obtaining [$^{18}F$]-labelled tracers for PET imaging (Schubiger el al, Eds "PET Chemistry: The Driving Force of Molecular Imaging" (In: Ernst Schering Res Found Workshop; 2007: 62); 2007 Springer GmbH).

$^{18}F^-$ is normally produced as an aqueous solution from the nuclear reaction $^{18}O(p,n)^{18}F$ by proton irradiation of [$^{18}O$] water (Ruth and Wolf, Radiochim. Acta 1979; 26: 21). It is well-known that $^{18}F^-$ in aqueous form is not very reactive and a number of manipulations are necessary in order to provide a reactive nucleophilic reagent. One important step is the addition of a cationic counterion (e.g. the cationic complex of Kryptofix and potassium or TBA+). Typically, the aqueous solution of $^{18}F^-$ is first adsorbed onto an anion exchange resin (Schlyer et al, Appl Rad Isotop 1990; 41: 531), followed by elution with an aqueous acetonitrile solution containing a carbonate salt such as $K_2CO_3$, or $KHCO_3$ accompanied by a cryptand such as Kryptofix™ ($K_{222}$) or tetrabutyl ammonium (Hamacher et al, J Nucl Med 1986; 27: 235; Brodack et al App Rad Isotop 1988; 39: 699). Alternatively, the $^{18}F^-$ can be eluted from the anion exchange column with the carbonate salt and addition of this to a solution of cryptand in acetonitrile as described by McConathy et al (Appl Rad Isotop 2003; 58: 657-666). Acetonitrile is the solvent of choice for the eluent solution primarily because of the excellent solubility of K[$^{18}F$]/Kryptofix or tetrabutylammonium $^{18}F^-$ therein. Also, given that the next step in making $^{18}F^-$ reactive generally involves use of acetonitrile to provide a lower boiling azeotrope for removal of water makes it sensible to use acetonitrile as the solvent in the step of adding the cationic counterion.

Use of these standard methods in the preparation of $^{18}F^-$ for the synthesis of various PET tracers is described in the art. In particular the use of acetonitrile in the step of adding a cationic counterion is a consistent feature, as described for example by Yu (Biomed Imaging Interven J 2006; 2(4): 1-11) in the synthesis of: 2-deoxy-2-[$^{18}F$]fluoroglucose ([$^{18}F$]-FDG, by Oh et al (Nuc Med Biol 2005; 32(8): 899-905) in the synthesis of 1-H-1-(3-[$^{18}F$]fluoro-2-hydroxypropyl)-2-nitroimidazole ([$^{18}F$]FMISO), by Oh et al (Nuc Med Biol 2004; 31: 803-809) in the synthesis of 3-deoxy-3-[$^{18}F$]fluorothymidine ($^{18}F$-FLT), by McConathy et al (Appl Rad Isotop 2003; 58: 657-666) in the synthesis of 1-amino-3-[$^{18}F$]fluorocyclobutane-1-carboxylic acid ([$^{18}F$]FACBC), by Kryza et al (Nuc Med Biol 2008, 35: 255-260) in the synthesis of [$^{18}F$]fluorocholine, by Ackennan et al (2011 J Label Comp Radiopharm; 54: 788-794) in the synthesis of 2-[(4-[$^{18}F$]Fluorobenzoyloxy)methyl]-1,4-naphthalenedione, and by Sun et al (Nuc Med Biol 2006; 33: 153-158) in the synthesis of sodium [$^{18}F$]fluoroacetate.

Traditionally, the eluent solution is freshly prepared on the day of synthesis, but modern positron emission tomography (PET) tracer manufacturers may for convenience prepare bulk solutions or pre filled vials for storage. The use of prefilled vials allows more well defined, reliable and reproducible synthesis processes (Hjelstuen et al, Eur J Pharm Biopharm 2011; 78: 307). In addition, prefilled vials can be made with a low bioburden and a documented shelf life, which serves as a better starting point for good manufacturing practice (GMP) quality manufacture compared to manually mixed solutions.

It is known that acetonitrile will hydrolyse at alkaline pH, forming acetamide and ammonium acetate in a two-step mechanism (Chin, Acc Chem Res 1991; 24: 145) as illustrated in FIG. 1:

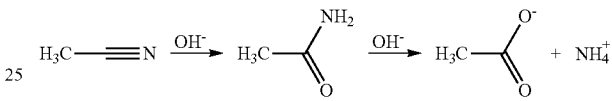

The rate constants for the above reaction are relatively low. Acetate is normally regarded as a weak nucleophile and should not pose any problem in $^{18}F$ labelling procedures. Also, acetamide is a known [$^{18}F$]fluoride labelling solvent and is not believed to negatively impact $^{18}F$ labelling reactions (Knust et al, J Radioanal Chem 1982; 74: 283, Knust et al, Appl Radiat Isot 1986; 37: 853).

The present inventors have however now observed that eluent solutions comprising acetonitrile used in the synthesis of [$^{18}F$]FACBC and [$^{18}F$]FDG generated mg/ml levels of acetamide and ammonium acetate during storage at room temperature or above, leading to previously unrecognised problems in the synthesis reactions. [$^{18}F$]FACBC synthesis was found to be affected by eluent degradation, with a reduction of RCY from 62.5% to 44.7% when the eluent solution was stored for 12 months at 30° C. The synthesis of [$^{18}F$]FDG was affected when the eluent was stored at 50° C., reducing RCY from 86.8% to 66.7% after 3 months of storage.

In light of these newly-recognised problems, there is a need to develop new strategies for the synthesis of $^{18}F$-labelled PET tracers.

SUMMARY OF THE INVENTION

The present invention provides a novel method for the preparation of $^{18}F$-fluoride ($^{18}F^-$) for use in radiofluorination reactions that has advantages over known methods. The method of the invention is particularly advantageous where bulk solutions are prepared and stored in prefilled vials rather than being freshly prepared on the day of synthesis. Also provided by the present invention is a radiofluorination reaction which comprises the method of the invention, as well as a cassette for use in carrying out the method of the invention and/or the radiofluorination method of the invention on an automated radiosynthesis apparatus.

DETAILED DESCRIPTION OF THE INVENTION

Figure 1:
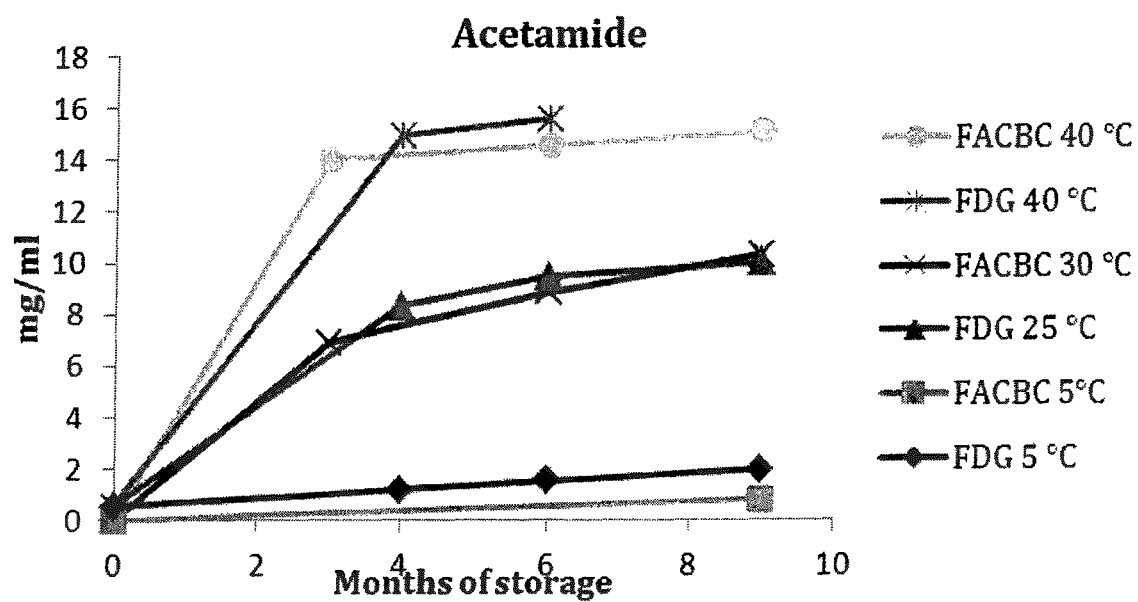
FIG. 1 is a graph showing acetamide generated in [$^{18}F$]FACBC and [$^{18}F$]FDG eluent vials during storage at 5° C., 25° C. and 40° C. (n=2-3).

In one aspect the present invention provides a method for preparation of $^{18}$F$^-$ for use in a radiofluorination reaction wherein said method comprises:
  (i) trapping an aqueous solution of $^{18}$F$^-$ onto an ion exchange column; and,
  (ii) passing an eluent solution through said ion exchange column on which said $^{18}$F$^-$ is adsorbed to obtain an $^{18}$F$^-$ eluent, wherein said eluent solution comprises a cationic counterion in a suitable solvent with the proviso that said eluent solution does not comprise acetonitrile.

The term "radiofluorination" in the context of the present invention refers to a radiochemical reaction for the production of an $^{18}$F-labelled compound wherein $^{18}$F$^-$ is reacted with a precursor compound comprising a substituent suitable for nucleophilic substitution with $^{18}$F$^-$.

The term "trapping" an aqueous solution of $^{18}$F$^-$ onto an ion exchange column refers to the process by which $^{18}$F$^-$ is retained on the ion exchange column. A suitable "ion exchange cartridge" in the context of the present invention is a solid-phase extraction (SPE) cartridge that retains $^{18}$F$^-$ and allows H$_2$$^{18}$O to pass through when an aqueous solution from the nuclear reaction $^{18}$O(p,n)$^{18}$F is passed through. Preferably, said ion-exchange cartridge is an anion exchange cartridge, most preferably a quaternary methylammonium (QMA) cartridge.

The term "$^{18}$F$^-$ eluent" refers to the solution comprising $^{18}$F$^-$ and the eluent solution obtained when the eluent solution is passed through the ion exchange column.

Said "eluent: solution" is free of acetonitrile, and preferably consists of said cationic counterion in said suitable solvent.

A "cationic counterion" in the context of the present invention is a positively-charged counterion that acts to improve the reactivity of $^{18}$F$^-$ when combined therewith. Examples of suitable cationic counterions for use in the method of the present invention include large but soft metal ions such as rubidium, caesium, potassium complexed with a cryptand, or tetraalkylammonium salts. A preferred cationic counterion is a metal complex of a cryptand, most preferably wherein said metal is potassium and wherein said cryptand is Kryptofix 222.

The "suitable solvent" for the eluent solution does not comprise any acetonitrile. Preferably, said suitable solvent is an alkanol, and is preferably ethanol or methanol, most preferably methanol. Said suitable solvent is either 100% alkanol, or is alternatively an "aqueous solution of an alkanol". For example said suitable solvent may comprise a ratio of alkanol:water in the range 60:40 to 100:0, preferably in the range 80:20 to 100:0 and most preferably 90:10 to 100:0. A certain amount of water can help with consistent elution of $^{18}$F$^-$ but it is preferable to have as little water as possible as the percentage of water is directly proportional to subsequent drying time.

The method of the invention is most advantageous where the eluent solution is for convenience prepared as a bulk solution and/or in prefilled vials for storage. As noted in the description of the prior art, use of prefilled vials permits more well defined, reliable and reproducible synthesis processes (Hjelstuen et al, Eur J Pharm Biopharm 2011, 78: 307), and prefilled vials can be made with a low bioburden and a documented shelf life, which serves as a better starting point for good manufacturing practice (GMP) quality manufacture compared to manually mixed solutions.

The method of the invention may optionally comprise the additional step:
  (iii) drying said $^{18}$F$^-$ eluted from said column in step (ii).

The term "drying" refers to the evaporation of the suitable solvent (as described above) to result in anhydrous $^{18}$F$^-$. This drying step is suitably carried out by application of heat and/or use of a solvent such as acetonitrile to provide a lower boiling azeotrope.

$^{18}$F-labelled PET tracers are conveniently prepared by means of an automated radiosynthesis apparatus. There are several commercially-available examples of such apparatus. An apparatus such as FASTlab™ (GE Healthcare) comprises a disposable cassette in which the radiochemistry is performed, which is fitted to the apparatus to perform the radiosynthesis.

In a preferred embodiment, the method of the present, invention is automated. Most preferably, the method of the present invention is carried out on a cassette suitable for use with an automated radiosynthesis apparatus.

The term "automated" refers to where a process is predominantly carried out using a machine or apparatus, i.e. comprising a minimal number of manual steps.

The term "cassette" refers to a disposable unit in which radiochemistry is performed. The cassette is fitted to an automated synthesis apparatus in order to perform a radiosynthesis and normally includes fluid pathways, a reaction vessel, and ports for receiving reagent vials as well as any solid-phase extraction cartridges used in post-radiosynthetic clean up steps. There are several commercially-available examples of "automated synthesis apparatus", including TRACERlab™ and FASTlab™ (GE Healthcare Ltd).

In another aspect, the present invention provides a radiofluorination reaction to obtain an $^{18}$F-labelled positron emission tomography (PET) tracer wherein said radiofluorination reaction comprises reaction of a precursor compound with $^{18}$F$^-$, wherein said precursor compound may comprise one or more protecting groups, and wherein said $^{18}$F$^-$ is obtained by the method as defined herein.

The suitable and preferred embodiments of any features of the method of the invention that are common to the radiofluorination reaction of the invention also apply to the radiofluorination reaction of the invention.

An "$^{18}$F-labelled PET tracer" is an $^{18}$F-labelled compound that when administered to a subject preferentially binds to a particular target within said subject in order that the target may be imaged by detecting emissions from $^{18}$F external to said subject using PET imaging. The term "PET imaging" refers to the nuclear medicine imaging technique that produces a three-dimensional image or picture of functional processes in the body. The technique detects pairs of gamma rays emitted indirectly by a positron-emitting radionuclide such as fluorine-18, which is introduced into the body as part of a PET tracer. Three-dimensional images of tracer concentration within the body are then constructed by computer analysis.

A "precursor compound" comprises a non-radioactive derivative of an $^{18}$F-labelled PET tracer designed so that chemical reaction with $^{18}$F$^-$ occurs site-specifically, can be conducted in the minimum number of steps (ideally a single step) and without the need for significant purification (ideally no further purification), to give the $^{18}$F-labelled PET tracer. Such precursor compounds are synthetic and can conveniently be obtained in good chemical purity.

Suitable "protecting groups" are well-known in the art and are discussed in more detail by Theodora W. Greene and Peter G. M. Wuts in "Protective Groups in Organic Synthesis" (Fourth Edition, John Wiley & Sons, 2007).

It will be appreciated by the skilled person that the inventive methods described herein can be applied for the preparation of any $^{18}$F-labelled PET tracer that can be prepared using nucleophilic radio fluorination with $^{18}$F$^-$. Non-limiting examples of such $^{18}$F-labelled PET tracers includes those set out in Table 1 below:

| $^{18}$F-labelled PET Tracer | Known Nucleophilic Method |
| --- | --- |
| 2-deoxy-2-[$^{18}$F]fluoro-D-glucose ([$^{18}$F]-FDG) | displacement of triflate |
| [$^{18}$F]fluorothymidine ([$^{18}$F]-FLT) | displacement of nosylate |
| [$^{18}$F]fluoronitroimidazole ([$^{18}$F]-FMISO) | displacement of tosylate |
| 6-[$^{18}$F]fluoroDOPA | aromatic substitution of nitro |
| [$^{18}$F]setoperone | aromatic substitution of nitro |
| [$^{18}$F]altanserin | aromatic substitution of nitro |
| [$^{18}$F]N-methylspiperone | aromatic substitution of nitro |
| 6-[$^{18}$F]fluorodopamine | aromatic substitution of 6-nitroperonal |
| (−)6-[$^{18}$F]fluoro-norepinephrine | aromatic substitution |
| 16α-[$^{18}$F]fluoroestradiol | displacement of an aliphatic cyclic sulfone |
| [$^{18}$F]fleroxacin | displacement of mesylate |
| [$^{18}$F]fluconazole | aromatic Schiemann reaction |
| 1-amino-3-[$^{18}$F]fluorocyclobutane-1-carboxylic acid ([$^{18}$F]-FACBC) | displacement of triflate |

The reactions listed in Table 1 above are common general knowledge in the art and are described for example in Chapter 14 of "Fluorine in Medicinal Chemistry and Chemical Biology" (Wiley 2009, Ojima. Ed), Chapter 6 of "Handbook of Radiopharmaceuticals: Radiochemistry and Applications (Wiley 2003, Welch and Redvanley, Eds), Chapter 6 of "Basic Sciences of Nuclear Medicine" (Springer 2011, Khalil, Ed) and in Chapter 10 of "Molecular Imaging: Radiopharmaceuticals for PET and SPECT" (Springer 2009, Vallabhajosula, Ed).

In a preferred embodiment, the $^{18}$F-labelled PET tracer is one of [$^{18}$F]FDG, [$^{18}$F]FMISO, [$^{18}$F]FLT and [$^{18}$F]FMISO, most preferably [$^{18}$F]FDG or [$^{18}$F]FACBC, and most especially preferably [$^{18}$F]FACBC.

In the experiments reported herein on storage of acetonitrile-based eluent solutions, it was found that the concentration of acetate was 3 times higher during labelling of [$^{18}$F]FACBC as compared with [$^{18}$F]FDG:

| FASTlab process step | Volume (μl) | Acetamide (μg/ml) | Acetate (μg/ml) |
| --- | --- | --- | --- |
| [$^{18}$F]FACBC synthesis | | | |
| Eluent vial | 1105 | 8700 | 3100 |
| Reactor before drying | 682 | 7320 | 2530 |
| Reactor during labelling | 1000 | 3495 | 1795 |
| End-product | 26000 | 0.2-0.5 | nm |
| [$^{18}$F]FDG synthesis | | | |
| Eluent vial | 825 | 8700 | 3100 |
| Reactor before drying | 377 | 6265 | 2120 |
| Reactor during labelling | 1600 | 844 | 597 |
| End-product | 15000 | 0.2-0.4 | nm |

As compared with [$^{18}$F]FDG, in the synthesis of [$^{18}$F]FACBC more eluent (1105 μl vs. 825 μl) and hence more acetate is introduced to the reaction vessel. The difference is enhanced during labelling because the volume used for labelling for [$^{18}$F]FACBC is smaller (1.0 ml vs. 1.6 ml). These coincidental factors like smaller volume of eluent and larger volume of labelling solvent made the synthesis of [$^{18}$F]FDG as described herein more resistant to eluent storage compared to the [$^{18}$F]FACBC reaction. It may well be that [$^{18}$F]FDG synthesis setups elsewhere could be more prone to eluent storage. This could be equally true in the case of other $^{18}$F-labelled PET tracers such as those listed above, and the present invention is thereby a solution that is easy to implement and is not detrimental on the quality of the eventual product.

It is most preferred that the radiofluorination reaction of the invention is automated, most preferably on an automated radiosynthesis apparatus as suitable and preferably described above.

In yet another aspect, the present invention provides a cassette for carrying out the radiofluorination reaction on an automated synthesis apparatus wherein said cassette comprises:
(i) an anion exchange column suitable for trapping an aqueous solution of $^{18}$F$^-$, wherein said anion exchange column is as defined herein;
(ii) a first vessel containing an eluent solution as defined herein;
(iii) a second vessel containing a precursor compound which upon reaction with $^{18}$F results in an $^{18}$F-labelled PET tracer as defined herein, wherein said
$^{18}$F$^-$ is obtained by the method as defined herein.

The suitable and preferred embodiments of any features of the method of the invention and/or the radiofluorination reaction of the invention that are common to the cassette of the invention also apply to the cassette of the invention.

BRIEF DESCRIPTION OF THE EXAMPLES

Example 1 describes an analysis of prior art eluent solutions that were stored.
Example 2 describes the synthesis of [$^{18}$F]FACBC and [$^{18}$F]FDG with stored vs. freshly-prepared prior art eluent.
Example 3 describes the synthesis of [$^{18}$F]FACBC with stored vs. freshly-prepared eluent of the present invention.

LIST OF ABBREVIATIONS USED IN THE EXAMPLES

ATR attenuated total reflectance
DTGS deuterated triglycine sulphate
[$^{18}$F]FACBC 1-amino-3-[$^{18}$F]fluorocyclobutane-1-carboxylic acid
[$^{18}$F]FDG 2-deoxy-2-[$^{18}$F]fluoro-D-glucose FT-IR Fourier transform infrared
K222 Kryptofix 222
MeCN acetonitrile
MeOH methanol
QMA quaternary methyl ammonium
RCY radiochemical yield
SPE solid-phase extraction
TLC thin layer chromatography
UV ultraviolet

EXAMPLES

All reagents and solvents were purchased from Merck and used without further purification. The [$^{18}$F]FDG precursor; 1,3,4,6-Tetra-O-acetyl-2-O-trifluoromethancsulfonyl-β-D-mannopyranose was purchased from ABX while the [$^{18}$F]FACBC precursor; Syn-1-(N-(tert-butoxycarbonyl)amino)-3-[[(trifluoromethyl)sulfonyl]oxy]-cyclobutane-1-carboxylic acid ethyl ester was obtained from GE Healthcare. The Oasis HLB plus cartridge and the Sep-Pak cartridges: QMA light Plus (K$_2$CO$_3$ form), tC18 light. Alumina N light were purchased from Waters (Milford, Mass., USA). A Capintec NaI ion chamber was used for all radioactive measurements (model CRC15R). Radio-thin layer chromatography (radio-TLC) was performed on a Packard instant imager using pre-coated plates of silica gel (Merck 60F$_{254}$).

Example 1

Storage of Prior Art Eluent Solutions 3.0 ml FASTlab eluent vials consisting of type-1 borosilicate glass (FIOLAX, MGlas AG, Münnerstadt, Germany), capped with a chlorobutyl stopper coated with Fluorotec® (West) and sealed with an aluminium cap after filling the eluent solution were used for the storage of two eluent solutions optimized for either [$^{18}$F]FACBC or [$^{18}$F]FDG synthesis The eluent solutions were as follows:

| Eluent composition | [$^{18}$F]FACBC | [$^{18}$F]FDG |
|---|---|---|
| K222 | 53.0 mg/ml | 53.0 mg/ml |
| K$_2$CO$_3$ | 7.3 mg/ml | 9.5 mg/ml |
| MeCN:H$_2$O | 79.5:20.5 (v/v) | 79.5:20.5 (v/v) |
| Fill volume | 1.105 ml | 0.825 ml |

The vials were stored in darkness in an up-right position using storage temperatures of 5, 25, 30, 40 and 50° C. Both eluents were stored over a nine-month period, during which time levels of acetamide and acetate were measured. Acetamide was quantified by infrared spectroscopy using a Perkin Elmer Spectrum 2000 Explorer FT-IR spectrometer with a DTGS detector and a single reflection diamond ATR (DuraSamplIR II from SensIR Technologies). Acetate was quantified by liquid chromatography with UV detection (Agilent 1100 series).

Figure 2:
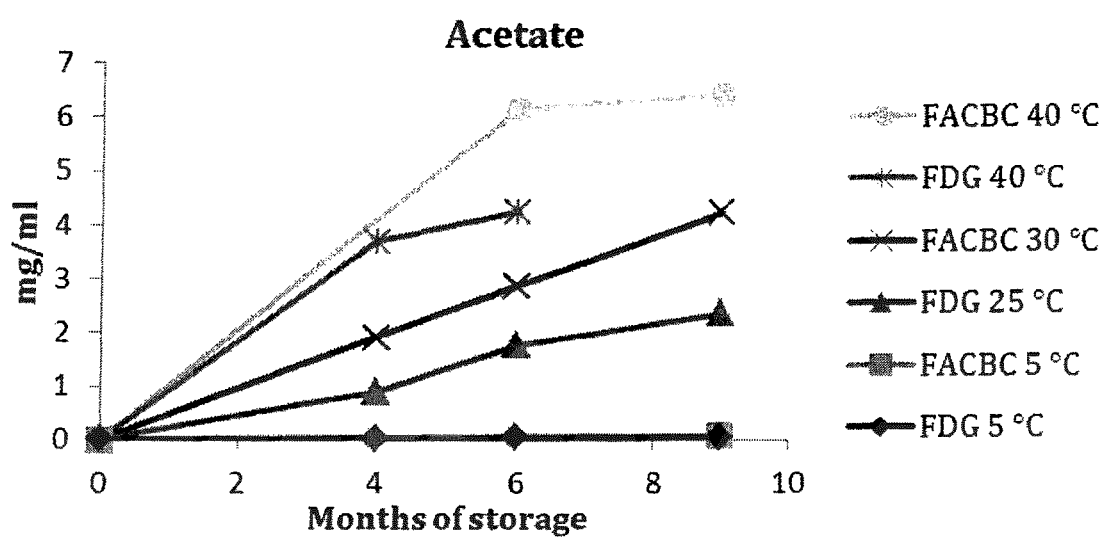
FIG. 2 is a graph showing acetate generated in [$^{18}$F] FACBC and [$^{18}$F]FDG eluent vials during storage at 5° C., 25° C. and 40° C. (n=2-3).

Notable levels (mg/ml) of acetamide and acetate were generated during a nine-month period of storage as seen in FIG. 1 (acetamide generated in FACBC and FDG eluent vials during storage at 5° C., 25° C. and 40° C.; n=2-3) and FIG. 2 (acetate generated m FACBC and FDG eluent vials during storage at 5° C., 25° C. and 40° C. n=2-3).

Example 2

Synthesis of [$^{18}$F]FACBC and [$^{18}$F]FDG with Stored vs. Freshly-prepared Prior Art Eluent The synthesis of [$^{18}$F]FACBC and [$^{18}$F]FDG was tested with both freshly prepared and stored eluents to investigate the impact of generated levels of acetamide and ammonium acetate on the RCY.

No-carrier-added [$^{18}$F]fluoride was produced via the $^{18}$O (p,n)$^{18}$F nuclear reaction on a GE PETtrace 6 cyclotron (Norwegian Cyclotron Centre, Oslo). Irradiations were performed using a dual-beam, 30 μA current on two equal Ag targets with HAVAR foils using 16.5 MeV protons. Each target contained 1.6 ml of ≥96% [$^{18}$O]water (Marshall Isotopes). Subsequent to irradiation and delivery to a hotcell, each target was washed with 1.6 ml of [$^{16}$O]water (Merck, water for GR analysis), giving approximately 2-5 Gbq in 3.2 ml of [$^{16}$O]water.

All radiochemistry was performed on a commercially available GE FASTlab™ with single-use cassettes. Each cassette is built around a one-piece-moulded manifold with 25 three-way stopcocks, all made of polypropylene. Briefly, the cassette includes a 5 ml reactor (cyclic olefin copolymer), one 1 ml syringe and two 5 ml syringes, spikes for connection with five prefilled vials, one water bag (100 ml) as well as various SPE cartridges and filters. Fluid paths are controlled with nitrogen purging, vacuum and the three syringes. The fully automated system is designed for single-step fluorinations with cyclotron-produced [$^{18}$F]fluoride. The FASTlab was programmed by the software package in a step-by-step time-dependent sequence of events such as moving the syringes, nitrogen purging, vacuum, and temperature regulation. Synthesis of [$^{18}$F]FDG and [$^{18}$F]FACBC were customized on separate cassettes, but both synthesis followed the three general steps: (a) [$^{18}$F]fluorination, (b) hydrolysis of protection groups and (c) SPE purification.

Prior Art Synthesis of [$^{18}$F]FDG

Vial A contained K222 (43.7 mg, 117 μmol), K$_2$CO$_3$ (7.8 mg, 56.7 μmol) in 79.5% (v/v) MeCN$_{(aq)}$ (825 μl). Vial B contained the precursor (39 mg, 81.2 μmol) in 2.0 ml of MeCN with 1700 ppm water. Vial C contained of MeCN (4.1 ml). Vial D contained 2 M NaOH (4.1 ml). Vial E contained 2.3 M phosphoric acid (4.1 ml). Aqueous [$^{18}$F]fluoride (1 ml, 100-200 Mbq) was passed through the QMA and into the $^{18}$O—H$_2$O recovery vial. The trapped [$^{18}$F]fluoride was eluted into the reactor using eluent from vial A (450 μl) and then concentrated to dryness by azeotropic distillation with acetonitrile (80 μl, vial C). Approximately 1.6 ml of precursor solution (corresponds to 31.2 mg; 65 μmol precursor) from vial B was added to the reactor and heated at 125° C. for 2 min. The reaction mixture was diluted with water and sent through the tC18 cartridge. Reactor was washed with water and sent through the tC18 cartridge. The labelled intermediate, fixed on the tC18 cartridge was first washed with water, then incubated with 2M NaOH (2.0 ml) for 2 min. The crude mixture was mixed with water (1.5 ml) and 2.3 M phosphoric acid (1.5 ml) and passed through the HLB and Alumina cartridges into the product vial made of glass (30 ml). Water (9 ml) was then sent through the HLB and Alumina cartridges and into the product vial. The purified formulation of [$^{18}$F]FDG contained a Final volume of 15 ml. Radiochemical purity was tested by radio-TLC using a mixture of MeCN:H$_2$O (95:5)

as the mobile phase. The radiochemical yield (RCY) was expressed as the amount of radioactivity in the [$^{18}$F]FDG fraction divided by the total used [$^{18}$F]fluoride activity (decay corrected). Total synthesis time was 22 min.

Prior Art Synthesis of [$^{18}$F]FACBC

Vial A contained $K_{222}$ (58.8 mg, 156 µmol), $K_2CO_3$ (8.4 mg, 60.8 µmol) in 79.5% (v/v) MeCN(aq) (1105 µl). Vial B contained 4 M HCl (2.0 ml). Vial C contained MeCN (4.1 ml). Vial D contained the precursor (48.4 mg, 123.5 µmol) in its dry form (stored at −20° C. until cassette assembly). Vial E contained 2 M NaOH (4.1 ml). The 30 ml product collection glass vial was filled with 200 mM citrate buffer (10 ml). Aqueous [$^{18}$F]fluoride (1-1.5 ml, 100-200 Mbq) was passed through the QMA and into the $^{18}$O—H$_2$O recovery vial. The QMA was then flushed with MeCN and sent to waste. The trapped [$^{18}$F]fluoride was eluted into the reactor using eluent from vial A (730 µl) and then concentrated to dryness by azeotropic distillation with acetonitrile (80 µl, vial C). Approximately 1.7 ml of MeCN was mixed with precursor in vial D from which 1.0 ml of the dissolved precursor (corresponds to 28.5 mg, 72.7 mmol precursor) was added to the reactor and heated for 3 min at 85° C. The reaction mixture was diluted with water and sent through the tC18 cartridge. Reactor was washed with water and sent through the tC18 cartridge. The labelled intermediate, fixed on the tC18 cartridge was washed with water, and then incubated with 2 M NaOH (2.0 ml) for 5 min. The labelled intermediate (without the ester group) was eluted off the tC18 cartridge into the reactor using water. The BOC group was hydrolysed by adding 4 M HCl (1.4 ml) and heating the reactor for 5 min at 60° C. The reactor content with the crude [$^{18}$F]FACBC was sent through the HLB and Alumina cartridges and into the 30 ml product vial. The HLB and Alumina cartridges were washed with water (9.1 ml total) and collected in the product vial. Finally, 2 M NaOH (0.9 ml) and water (2.1 ml) was added to the product vial, giving the purified formulation of [$^{18}$F]FACBC with a total volume of 26 ml. Radiochemical purity was measured by radio-TLC using a mixture of MeCN:MeOH:H$_2$O:CH$_3$COOH (20:5:5:1) as the mobile phase. The radiochemical yield (RCY) was expressed as the amount of radioactivity in the [$^{18}$F]FACBC fraction divided by the total used [$^{18}$F]fluoride activity (decay corrected). Total synthesis time was 43 min.

Using freshly prepared eluents, RCY of [$^{18}$F]FACBC and [$^{18}$F]FDG were 62.5%±1.93 (SD), n=4 and 86.8%±1.25 (SD), n=9 respectively.

Figure 3:
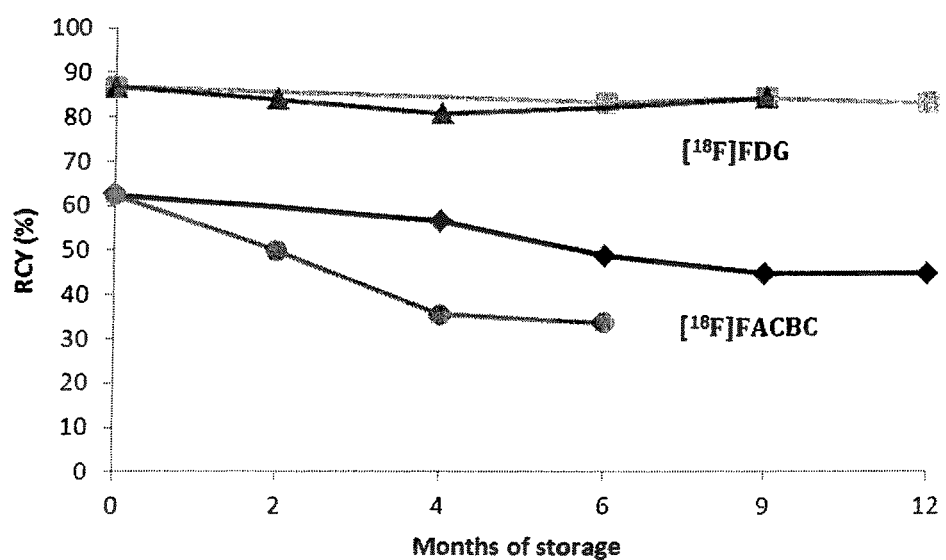
FIG. 3 shows the RCY of [$^{18}$F]FACBC after eluent stored at 30° C. (●), 40° C. (◆) and RCY of [$^{18}$F]FDG after eluent stored at eluent at 25° C. (■), 40° C. (▲).

When the FACBC eluent was stored at 30 or 40° C., a decrease in RCY with increasing storage time was observed as shown in FIG. 3, which shows the RCY of [$^{18}$F]FACBC after eluent stored at 30° C. (●), 40° C. (♦) and RCY of [$^{18}$F]FDG after eluent stored at eluent at 25° C. (■), 40° C. (▲). The RCY of [$^{18}$F]FACBC dropped from 62.5% to 44.7% when the FACBC eluent was stored at 30° C. for 12 months and from 62.5% to 33.6% when stored at 40° C. for 6 months. It was therefore observed a negative correlation between degradation of acetonitrile and reduction in RCY of [$^{18}$F]FACBC. The RCY for [$^{18}$F]FDG was observed to fall from 86.8% to 66.7% for [$^{18}$F]FDG when the eluent solution was stored at 50° C. for 3 months (n=3).

Example 3

Figure 4:
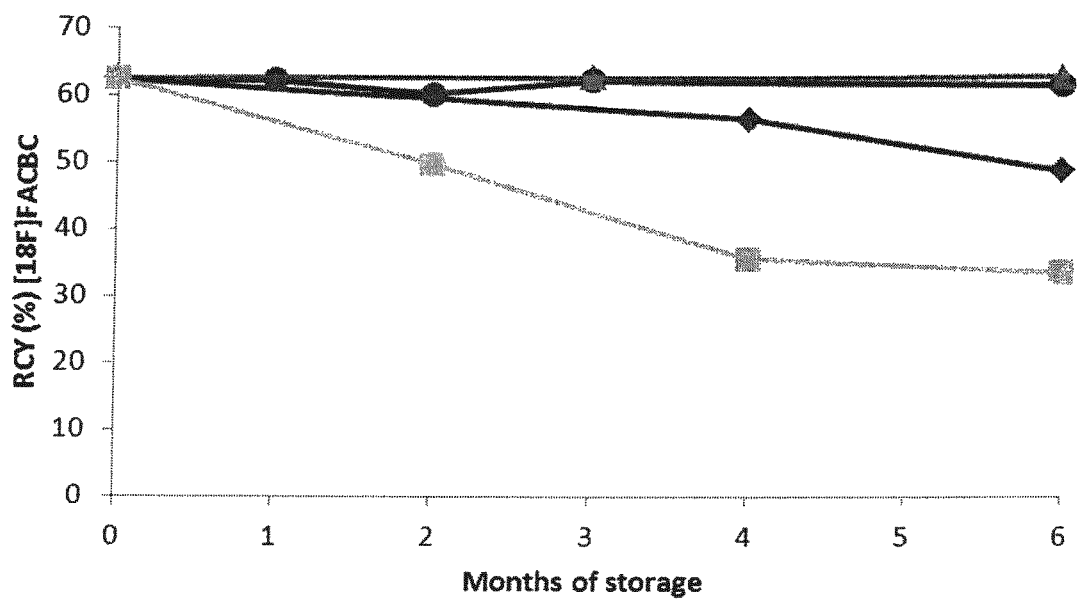
FIG. 4 illustrates the RCY of [$^{18}$F]FACBC after eluent with methanol (MeOH) stored at 30° C. (▲), 50° C. (●) and RCY of [$^{18}$F]FDG after eluent with acetonitrile (MeCN) stored at eluent at 30° C. (◆), 40° C. (■).

Synthesis of f [$^{18}$F]FACBC with Stored vs. Freshly-prepared Eluent of the Present Invention FACBC eluent vials in which acetonitrile was replaced by methanol was stored for predetermined time points and tested in the synthesis of [$^{18}$F]FACBC. FIG. 4 illustrates the RCY of [$^{18}$F]FACBC after eluent with MeOH stored at 30° C. (▲), 50° C. (●) and RCY of [$^{18}$F]FDG after eluent with MeCN stored at eluent at 30° C. (♦), 40° C. (■). While the acetonitrile based eluent resulted in a gradual decrease in RCY with increasing storage time, the RCY remained unchanged with the methanol-based eluent even when stored at 50° C. for 6 months.

What is claimed is:

1. A method for preparation of an an [$^{18}$F]FACBC radiotracer on a cassette within an automated radiosynthesis apparatus, wherein said method comprises:
   (i) trapping an aqueous solution of $^{18}$F$^-$ onto an anion exchange column on the cassette of the automated radiosynthesis apparatus;
   (ii) passing an eluent solution from a bulk solution or a prefilled vial of the cassette through said anion exchange column on which said $^{18}$F— is adsorbed to obtain an $^{18}$F$^-$ eluent, the eluent solution comprising a mixture of potassium carbonate and 4,7,13,16,21,24-hexaoxa-1,10-diazabicyclo[8.8.8]hexacosane in an aqueous alkanol solvent and being devoid of acetonitrile;
   (iii) drying the $^{18}$F$^-$ eluent eluted from the column in step (ii) in the presence of acetonitrile;
   (iv) reacting the 18F— with a precursor followed by removal of protecting groups in the automated radiosynthesis apparatus to obtain the [$^{18}$F]FACBC; and
   (v) purification of the [$^{18}$F]FACBC using solid phase extraction;
   wherein said eluent solution is capable of being (i) prepared in bulk and (ii) stored in a plurality of vials prior to use, thereby affording a consistent percentage radiochemical yield of the [$^{18}$F]FACBC when used in a plurality of subsequent radiofluorination reactions over time.

2. The method as defined in claim 1, wherein said anion exchange column is a quaternary methylammonium (QMA) column.

3. The method as defined in claim 1, wherein the alkanol solvent is aqueous methanol having a ratio of methanol to water greater than about 79.5:20.5.

4. The method as defined in claim 1, wherein the alkanol solvent is aqueous methanol having a ratio of methanol to water greater than 90:10.

5. A method for preparation of an [$^{18}$F]FACBC radiotracer on a cassette within an automated radiosynthesis apparatus, wherein said method comprises:
   (i) trapping an aqueous solution of $^{18}$F$^-$ onto a quaternary methylammonium (QMA) column on the cassette of the automated radiosynthesis apparatus;
   (ii) passing an eluent solution from a bulk solution or a prefilled vial of the cassette through said anion exchange column on which said $^{18}$F— is adsorbed to obtain an $^{18}$F$^-$ eluent, the eluent solution comprising a mixture of 4,7,13,16,21,24-hexaoxa-1,10-diazabicyclo [8.8.8]hexacosane and $K_2CO_3$ in an aqueous methanol solvent and being devoid of acetonitrile;
   (iii) drying the $^{18}$F$^-$ eluent eluted from the column in step (ii) in the presence of acetonitrile;
   (iv) reacting the 18F— with a precursor followed by removal of protecting groups in the automated radiosynthesis apparatus to obtain the [$^{18}$F]FACBC; and
   (v) purification of the [$^{18}$F]FACBC in the automated radiosynthesis apparatus using solid phase extraction;
   wherein said eluent solution is capable of being (i) prepared in bulk and (ii) stored in a plurality of vials prior to use, thereby affording a consistent percentage radiochemical yield of the [$^{18}$F]FACBC when used in a plurality of subsequent radiofluorination reactions over time.

6. The method as defined in claim 5, wherein the aqueous methanol solvent has ratio of methanol to water greater than about 79.5:20.5.

7. The method as defined in claim 5, wherein the aqueous methanol solvent has ratio of methanol to water greater than 90:10.

8. The method as defined in claim 1, wherein the eluent solution is provided in a prefilled vial of the cassette.

9. The method as defined in claim 5, wherein the eluent solution is provided in a prefilled vial of the cassette.

* * * * *